(12) United States Patent
Tobinick

(10) Patent No.: US 8,119,127 B2
(45) Date of Patent: *Feb. 21, 2012

(54) CYTOKINE ANTAGONISTS FOR NEUROLOGICAL AND NEUROPSYCHIATRIC DISORDERS

(75) Inventor: Edward L Tobinick, Los Angeles, CA (US)

(73) Assignee: Tact IP, LLC

( * ) Notice: Subject to any disclaimer, the term of this patent is extended or adjusted under 35 U.S.C. 154(b) by 326 days.

This patent is subject to a terminal disclaimer.

(21) Appl. No.: 11/262,528

(22) Filed: Oct. 28, 2005

(65) Prior Publication Data

US 2006/0051381 A1 Mar. 9, 2006

Related U.S. Application Data

(60) Division of application No. 10/269,745, filed on Oct. 9, 2002, now Pat. No. 6,982,089, which is a continuation-in-part of application No. 10/236,097, filed on Sep. 6, 2002, now abandoned, which is a continuation-in-part of application No. 09/841,844, filed on Apr. 25, 2001, now Pat. No. 6,537,549, which is a continuation-in-part of application No. 09/826,976, filed on Apr. 5, 2001, now Pat. No. 6,419,944, which is a continuation-in-part of application No. 09/666,068, filed on Dec. 11, 2000, now Pat. No. 6,379,666, which is a division of application No. 09/476,643, filed on Dec. 31, 1999, now Pat. No. 6,177,077, which is a continuation-in-part of application No. 09/275,070, filed on Mar. 23, 1999, now Pat. No. 6,015,557, which is a continuation-in-part of application No. 09/256,388, filed on Feb. 24, 1999, now abandoned.

(51) Int. Cl.
*A61K 39/395* (2006.01)
(52) U.S. Cl. .................................................. 424/130.1
(58) Field of Classification Search .................... None
See application file for complete search history.

(56) References Cited

U.S. PATENT DOCUMENTS

| | | | |
|---|---|---|---|
| 5,656,272 A | 8/1997 | Le et al. | |
| 5,698,195 A | 12/1997 | Le et al. | |
| 5,919,452 A | 7/1999 | Le et al. | |
| 5,958,409 A | 9/1999 | Turk et al. | |
| 6,015,557 A * | 1/2000 | Tobinick et al. | 424/134.1 |
| 6,177,077 B1 * | 1/2001 | Tobinick | 424/134.1 |
| 6,277,969 B1 | 8/2001 | Le et al. | |
| 6,284,471 B1 | 9/2001 | Le et al. | |
| 6,306,820 B1 | 10/2001 | Bendele et al. | |
| 6,419,944 B2 * | 7/2002 | Tobinick | 424/422 |
| 6,537,549 B2 * | 3/2003 | Tobinick | 424/134.1 |
| 6,548,527 B2 * | 4/2003 | Rahman et al. | 514/378 |
| 6,635,250 B2 | 10/2003 | Olmarker et al. | |
| 6,649,589 B1 | 11/2003 | Olmarker et al. | |
| 6,835,823 B2 | 12/2004 | Le et al. | |
| 6,982,089 B2 * | 1/2006 | Tobinick | 424/400 |
| 6,991,791 B2 | 1/2006 | Le et al. | |
| 7,115,557 B2 | 10/2006 | Olmarker | |
| 7,214,658 B2 * | 5/2007 | Tobinick | 514/2 |
| 7,608,262 B2 | 10/2009 | Elliott | |
| 2008/0019964 A1 | 1/2008 | Olmarker et al. | |
| 2008/0019969 A1 | 1/2008 | Gorman | |
| 2008/0019970 A1 | 1/2008 | Gorman | |
| 2008/0019975 A1 | 1/2008 | Gorman | |
| 2008/0085274 A1 | 4/2008 | Olmarker et al. | |
| 2008/0213283 A1 | 9/2008 | Olmarker et al. | |

FOREIGN PATENT DOCUMENTS

| | | |
|---|---|---|
| SE | 9803276 | 9/1998 |
| SE | 9803710 | 10/1998 |
| SE | 99/01671 | 9/1999 |

OTHER PUBLICATIONS

Yasutake et al. (Eur Arch Psychiat Clin Neurosc 256: 402-406, 2006.*
Lanzrein et al., Alz Dis Assoc Disord. 12: 215-227, 1998.*
Jellinger, Curr Alz Res 3: 377-391, 2006.*
Halliday et al Clin Exp Pharmacol Physiol 27: 1-8, 2000.*
Steece-Collier et al., PNAS USA 99(22): 13972-13974, 2002.*
Feigin et al., Curr Opin Neurol 15: 483-489, 2002.*
Tobinick and Britschgi-Davoodifar, Swiss Med Weekly—9 pages.*
Bohac et al. Neurobiol Aging 23 (1), Supp [1]; pp. S83-S83, 2002, MA 315.*
Tobinick MedGenMed Medscape Gen Med 8(2) srn. 25, 2006 (pp. 1-10).*

(Continued)

*Primary Examiner* — Daniel E Kolker
*Assistant Examiner* — Aditi Dutt
(74) *Attorney, Agent, or Firm* — Neifeld IP Law, P.C.

(57) ABSTRACT

Methods for treating neurological or neuropsychiatric diseases or disorders in humans by administering to the human a therapeutically effective dose of specific biologics are presented. The biologics of consideration include antagonists of tumor necrosis factor or of interleukin-1. The administration of these biologics is performed by specific methods, most, but not all of which fall into the category of anatomically localized administration designed for perispinal use. Anatomically localized administration involving perispinal use includes, but is not limited to the subcutaneous, intramuscular, interspinous, epidural, peridural, parenteral or intrathecal routes. Additionally, intranasal administration is discussed as a method to provide therapeutic benefit.

The clinical conditions of consideration include, but are not limited to the following: diseases of the brain, including neurodegenerative diseases such as Alzheimer's Disease and Parkinson's Disease; migraine headache; spinal radiculopathy associated with intervertebral disc herniation, post-herpetic neuralgia, reflex sympathetic dystrophy, neuropathic pain, vertebral disc disease, low back pain, amyotrophic lateral sclerosis, chronic fatigue syndrome; and neuropsychiatric diseases, including bipolar affective disorder, anorexia nervosa, nicotine withdrawal, narcotic addiction, alcohol withdrawal, post-partum depression, and schizoaffective illness.

2 Claims, No Drawings

OTHER PUBLICATIONS

Valdueza et al. the Lancet, 355: 200-201, 2000.*
Tobinick, Curr Alz Res 4: 550-552, 2007.*
Griffin et al. J Neuroinflamm 5: 1-3, 2008.*
Kaufman KR, Int Clin Psychopharm 20: 239-241, 2005—abstract only.*
Mohan et al. Arthritis Rheum 44: 2862-2869, 2001—abstract only.*
Abraham, E, et al., *Lenercept(p55 tumor necrosis factor receptor fusion protein) in severe sepsis and early septic shock: A randomized, double-blind, placebo-controlled, multicenter phase III trial with 1,342 patients*. Crit Care Med 2001 vol. 29, No. 3, p. 503-510.
Aisen, P.S. and K.L. Davis, *Inflammatory mechanisms in Alzheimer's disease: implications for therapy*. Am J Psychiatry, 1994. 151(8): p. 1105-1113.
Aisen, P.S. and K.L. Davis, *The search for disease-modifying treatment for Alzheimer's disease*. Neurology, 1997. 48(5 Suppl 6): p. S35-41.
Aisen, P.S., K.L. Davis, J.D. Berg, K. Schafer, K. Campbell, R.G. Thomas, M.F. Weiner, M.R. Farlow, M. Sano, M. Grundman, and L.J. Thal, *A randomized controlled trial of prednisone in Alzheimer's disease. Alzheimer's Disease Cooperative Study*. Neurology, 2000. 54(3): p. 588-593.
Al Saieg, N. and M.J. Luzar, *Etanercept induced multiple sclerosis and transverse myelitis*. J Rheumatol, 2006. 33(6): p. 1202-1204.
Alvarez, X.A., A. Franco, L. Femandez-Novoa, and R. Cacabelos, *Blood levels of histamine, IL-1 beta, and TNF-alpha in patients with mild to moderate Alzheimer disease*. Mol Chem Neuropathol, 1996. 29(2-3): p. 237-52.
Anderson, R., *Diodrast studies of the vertebral and cranial venous systems to show their probable role in cerebral metastases*. J Neurosurg, 1951. 8(4): p. 411-22.
Anthony, J.C., J.C.S. Breitner, P.P. Zandi, M.R. Meyer, I. Jurasova, M.C. Norton, and S.V. Stone, *Reduced prevalence of AD in users of NSAIDs and H2 receptor antagonists: the Cache County study*. Neurology, 2000. 54(11): p. 2066-71.
Apkarian, A.V., Y. Sosa, S. Sonty, R.M. Levy, R.N. Harden, T.B. Parrish, and D.R. Gitelman, *Chronic back pain is associated with decreased prefrontal and thalamic gray matter density*. J Neurosci, 2004. 24(46): p. 10410-5.
Banks, W.A., *Are the extracellular [correction of extracelluar] pathways a conduit for the delivery of therapeutics to the brain?* Curr Pharm Des, 2004. 10(12): p. 1365-70.
Banks, W.A., S.R. Plotkin, and A.J. Kastin, *Permeability of the blood-brain barrier to soluble cytokine receptors*. Neuroimmunomodulation, 1995. 2(3): p. 161-5.
Barger, S.W., D. Horster, K. Furukawa, Y. Goodman, J. Krieglstein, and M.P. Mattson, *Tumor necrosis factors alpha and beta protect neurons against amyloid beta-peptide toxicity: evidence for involvement of a kappa B-binding factor and attenuation of peroxide and Ca2+ accumulation*. Proc Natl Acad Sci U S A, 1995. 92(20): p. 9328-32.
Batson, O.V., *The Function of the Vertebral Veins and their role in the spread of metastases*. Annals of Surgery, 1940. 112: p. 138-149.
Batson, O.V., *The Vertebral Vein System, Caldwell Lecture*, 1956. American Journal of Roentgenology, 1957. 78(2).
Bensouda-Grimaldi, L., D. Mulleman, J.P. Valat, and E. Autret-Leca, *Adalimumab-associated multiple sclerosis*. J Rheumatol, 2007. 34(1): p. 239-40; discussion 240.
Bjornberg, F. et al., *Mechanisms Involved in the Process of the p55 and the p75 Tumor Necrosis Factor(TNF) Receptors to Soluble Receptor Forms*. Lymphokine and Cytokine Research, vol. 13, No. 3, 1994, p. 203-211.
Breitner, J.C., *The role of anti-inflammatory drugs in the prevention and treatment of Alzheimer's disease*. Annu Rev Med, 1996. 47: p. 401-11.
Brisby, H., K. Olmarker, K. Larsson, M. Nutu, and B. Rydevik, *Proinflammatory cytokines in cerebrospinal fluid and serum in patients with disc herniation and sciatica*. Eur Spine J, 2002. 11(1): p. 62-6.
Burkovetskaya, M.E., S.G. Levin, and O.V. Godukhin, *Neuroprotective effects of interleukin-10 and tumor necrosis factor-alpha against hypoxia-induced hyperexcitability in hippocampal slice neurons*. Neurosci Lett, 2007. 416(3): p. 236-40.
Byrod, G., K. Olmarker, S. Konno, K. Larsson, K. Takahashi, and B. Rydevik, *A rapid transport route between the epidural space and the intraneural capillaries of the nerve roots*. Spine, 1995. 20(2): p. 138-43.
Byrod, G., B. Rydevik, B.R. Johansson, and K. Olmarker, *Transport of epidurally applied horseradish peroxidase to the endoneurial space of dorsal root ganglia: a light and electron microscopic study*. J Peripher Nerv Syst, 2000. 5(4): p. 218-26.
Cacabelos, R., X.A. Alvarez, A. Franco-Maside, L. Femandez-Novoa, and J. Caamano, *Serum tumor necrosis factor(TNF) in Alzheimer's disease and multi-infarct dementia*. Methods Find Exp Clin Pharmacol, 1994. 16(1): p. 29-35.
Carlson, N.G., A. Bacchi, S.W. Rogers, and L.C. Gahring, *Nicotine blocks TNF-alpha-mediated neuroprotection to NMDA by an alpha-bungarotoxin-sensitive pathway*. J Neurobiol, 1998. 35(1): p. 29-36.
Chauhan, N.B. and G.J. Siegel, *Intracerebroventricular passive immunization with anti-Abeta antibody in Tg2576*. J Neurosci Res, 2003. 74(1): p. 142-7.
Chauhan, N.B. and G.J. Siegel, *Efficacy of anti-Abeta antibody isotypes used for intracerebroventricular immunization in TgCRND8*. Neurosci Lett, 2005. 375(3): p. 143-7.
Cooper, N.R., R.N. Kalaria, P.L. McGeer, and J. Rogers, *Key issues in Alzheimer's disease inflammation*. Neurobiol Aging, 2000. 21(3): p. 451-453.
Dolga, A.M., I. Granic, T. Blank, H.G. Knaus, J. Spiess, P.G. Luiten, U.L. Eisel, and I.M. Nijholt, *TNF-alpha-mediates neuroprotection against glutamate-induced excitotoxicity via NF-kappaB-dependent up-regulation of K2.2 channels*. J Neurochem, 2008. 107(4): p. 1158-67.
Edsbagge, M., M. Tisell, L. Jacobsson, and C. Wikkelso, *Spinal CSF absorption in healthy individuals*. Am J Physiol Regul Integr Comp Physiol, 2004. 287(6): p. R1450-5.
Edwards, M.M. and S.R. Robinson, TNF alpha affects the expression of GFAP and S100B: implications for Alzheimer's disease. J Neural Transm, 2006. 113(11): p. 1709-15.
Engelborghs, S., M. De Brabander, J. De Cree, R. D'Hooge, H. Geerts, H. Verhaegen, and P.P. De Deyn, *Unchanged levels of interleukins, neopterin, interferon-gamma and tumor necrosis factor-alpha in cerebrospinal fluid of patients with dementia of the Alzheimer type*. Neurochem Int, 1999. 34(6): p. 523-30.
Figiel, I., Pro-inflammatory cytokine TNF-alpha as a neuroprotective agent in the brain. Acta Neurobiol Exp (Wars), 2008. 68(4): p. 526-34.
Fillit, H., W.H. Ding, L. Buee, J. Kalman, L. Altstiel, B. Lawlor, and G. Wolf-Klein, *Elevated circulating tumor necrosis factor levels in Alzheimer's disease*. Neurosci Lett, 1991. 129(2): p. 318-20.
Fontaine, V., S. Mohand-Said, N. Hanoteau, C. Fuchs, K. Pfizenmaier, and U. Eisel, *Neurodegenerative and neuroprotective effects of tumor Necrosis factor(TNF) in retinal ischemia: opposite roles of TNF receptor 1 and TNF receptor 2*. J Neurosci, 2002. 22(7): p. RC216.
Furst, D.E, et al., *Intravenous Human Recombinant Tumor Necrosis Factor Receptor p55-Fc IgG1 Fusion Protein, Ro 45-2081(Lenercept): Results of a Dose-Finding Study in Rheumatoid Arthritis*. The Journal of Rheumatology, 2003; 30:10, p. 2123-2126.
Gallo, P., M.G. Piccinno, L. Krzalic, and B. Tavolato, *Tumor necrosis factor alpha(TNF alpha) and neurological diseases. Failure in detecting TNF alpha in the cerebrospinal fluid from patients with multiple sclerosis, AIDS dementia complex, and brain tumours*. J Neuroimmunol, 1989. 23(1): p. 41-4.
Genevay, S., S. Stingelin, and C. Gabay, *Efficacy of etanercept in the treatment of acute, severe sciatica: a pilot study*. Ann Rheum Dis, 2004. 63(9): p. 1120-3.
Gisolf, J., J.J. van Lieshout, K. van Heusden, F. Pott, W.J. Stok, and J.M. Karemaker, *Human cerebral venous outflow pathway depends on posture and central venous pressure*. J Physiol, 2004. 560(Pt 1): p. 317-27.
Glabinski, A.R., B. Bielecki, J.A. Kawczak, V.K. Tuohy, K. Selmaj, and R.M. Ransohoff, *Treatment with soluble tumor necrosis factor receptor(sTNFR):Fc/p80 fusion protein ameliorates relapsing-remitting experimental autoimmune encephalomyelitis and decreases chemokine expression. Autoimmunity, 2004. 37(6-7): p. 465-71.

Goiriz, R., et al., *Flare and change of psoriasis morphology during the course of treatment with tumour necrosis factor blockers.* Clinical and Experimental Dermatology, 32, 176-179, 2006.

Gomez-Gallego, M., J. Meca-Lallana, and A. Fernandez-Barreiro, *Multiple sclerosis onset during etanercept treatment.* Eur Neurol, 2008. 59(1-2): p. 91-3.

Goodman, J.C., C.S. Robertson, R.G. Grossman, and R.K. Narayan, *Elevation of tumor necrosis factor in head injury.* J Neuroimmunol, 1990. 30(2-3): p. 213-7.

Griffin, W.S., *Perispinal etanercept: potential as an Alzheimer therapeutic.* J Neuroinflammation, 2008. 5: p. 3.

Groen, R.J., D.F. du Toit, F.M. Phillips, P.V. Hoogland, K. Kuizenga, M.H. Coppes, C.J. Muller, M. Grobbelaar, and J. Mattyssen, *Anatomical and pathological considerations in percutaneous vertebroplasty and kyphoplasty: a reappraisal of the vertebral venous system.* Spine, 2004. 29(13): p. 1465-71.

Hale, K.K, et al., *Multifunctional Regulation of the Biological Effects of TNF-α by the Soluble Type I and Type II TNF Receptors.* Cytokine, vol. 7, 1995; pp. 26-38.

Heldmann, U., P. Thored, J.H. Claasen, A. Arvidsson, Z. Kokaia, and O. Lindvall, *TNF-alpha antibody infusion impairs survival of stroke-generated neuroblasts in adult rat brain.* Exp Neurol, 2005. 196(1): p. 204-8.

Hofman, F.M., D.R. Hinton, K. Johnson, and J.E. Merrill, *Tumor necrosis factor identified in multiple sclerosis brain.* J Exp Med, 1989. 170(2): p. 607-12.

Hulse, R.E., W.G. Swenson, P.E. Kunkler, D.M. White, and R.P. Kraig, *Monomeric IgG is neuroprotective via enhancing microglial recycling endocytosis and TNF-alpha.* J Neurosci, 2008. 28(47): p. 12199-211.

Ibukuro, K., H. Fukuda, K. Mori, and Y. Inoue, *Topographic anatomy of the vertebral venous system in the thoracic inlet.* AJR Am J Roentgenol, 2001. 176(4): p. 1059-65.

Igarashi, A., S. Kikuchi, S. Konno, and K. Olmarker, *Inflammatory cytokines released from the facet joint tissue in degenerative lumbar spinal disorders.* Spine, 2004. 29(19): p. 2091-5.

Klegeris, A., D.G. Walker, and P.L. McGeer, *Interaction of Alzheimer beta-amyloid peptide with the human monocytic cell line THP-1 results in a protein kinase C-dependent secretion of tumor necrosis factor-alpha.* Brain Res, 1997. 747(1): p. 114-21.

Klinkert, W.E., K. Kojima, W. Lesslauer, W. Rinner, H. Lassmann, and H. Wekerle, *TNF-alpha receptor fusion protein prevents experimental auto-immune encephalomyelitis and demyelination in Lewis rats: an overview.* J Neuroimmunol, 1997. 72(2): p. 163-8.

Knoblach, S.M., L. Fan, and A.I. Faden, *Early neuronal expression of tumor necrosis factor-alpha after experimental brain injury contributes to neurological impairment.* J Neuroimmunol, 1999. 95(1-2): p. 115-25.

Koopman, W.J, et al. *Rheumatoid Arthritis: Anticytokine Therapies on the Horizon,* vol. 128, Issue 3; pp. 231-233, Feb. 1998.

Larsson, K., B. Rydevik, and K. Olmarker, *Disc related cytokines inhibit axonal outgrowth from dorsal root ganglion cells in vitro.* Spine, 2005. 30(6): p. 621-4.

Laws, S.M., R. Perneczky, S. Wagenpfeil, U. Muller, H. Forstl, R.N. Martins, A. Kurz, and M. Riemenschneider, *TNF polymorphisms in Alzheimer disease and functional implications on CSF beta-amyloid levels.* Hum Mutat, 2005. 26(1): p. 29-35.

Lirk, P., C. Kolbitsch, G. Putz, J. Colvin, H.P. Colvin, I. Lorenz, C. Keller, L. Kirchmair, J. Rieder, and B. Moriggl, *Cervical and high thoracic ligamentum flavum frequently fails to fuse in the midline.* Anesthesiology, 2003. 99(6): p. 1387-90.

Lirk, P., B. Moriggl, J. Colvin, C. Keller, L. Kirchmair, J. Rieder, and C. Kolbitsch, *The incidence of lumbar ligamentum flavum midline gaps.* Anesth Analg, 2004. 98(4): p. 1178-80, table of contents.

Maness, L.M., W.A. Banks, J.E. Zadina, and A.J. Kastin, *Selective transport of blood-borne interleukin-1 alpha into the posterior division of the septum of the mouse brain.* Brain Res, 1995. 700(1-2): p. 83-8.

Marchetti, L., M. Klein, K. Schlett, K. Pfizenmaier, and U.L. Eisel, *Tumor necrosis factor(TNF)-mediated neuroprotection against glutamate-induced excitotoxicity is enhanced by N-methyl-D-aspartate receptor activation. Essential role of a TNF receptor 2-mediated phosphatidylinositol 3-kinase-dependent NF-kappa B pathway.* J Biol Chem, 2004. 279(31): p. 32869-81.

Masseguin, C., L. Mani-Ponset, S. Herbute, A. Tixier-Vidal, and J. Gabrion, *Persistence of tight junctions and changes in apical structures and protein expression in choroid plexus epithelium of rats after short-term head-down tilt.* J Neurocytol, 2001. 30(5): p. 365-77.

Mastroianni, C.M., F. Paoletti, C. Valenti, V. Vullo, E. Jirillo, and S. Delia, *Tumour necrosis factor(TNF-alpha) and neurological disorders in HIV infection.* J Neurol Neurosurg Psychiatry, 1992. 55(3): p. 219-21.

Mattson, M.P., S.W. Barger, K. Furukawa, A.J. Bruce, T. Wyss-Coray, R.J. Mark, and L. Mucke, *Cellular signaling roles of TGF beta, TNF alpha and beta APP in brain injury responses and Alzheimer's disease.* Brain Res Brain Res Rev, 1997. 23(1-2): p. 47-61.

McGeer, P.L., M. Schulzer, and E.G. McGeer, *Arthritis and anti-inflammatory agents as possible protective factors for Alzheimer's disease: a review of 17 epidemiologic studies.* Neurology, 1996. 47(2): p. 425-32.

Medeiros, R., R.D. Prediger, G.F. Passos, P. Pandolfo, F.S. Duarte, J.L. Franco, A.L. Dafre, G. Di Giunta, C.P. Figueiredo, R.N. Takahashi, M.M. Campos, and J.B. Calixto, *Connecting TNF-alpha signaling pathways to iNOS expression in a mouse model of Alzheimer's disease: relevance for the behavioral and synaptic deficits induced by amyloid beta protein.* J Neurosci, 2007. 27(20): p. 5394-404.

Mohan, N., E.T. Edwards, T.R. Cupps, P.J. Oliverio, G. Sandberg, H. Crayton, J.R. Richert, and J.N. Siegel, *Demyelination occurring during anti-tumor necrosis factor alpha therapy for inflammatory arthritides.* Arthritis Rheum, 2001. 44(12): p. 2862-9.

Mohler, K.M., D.S. Torrance, C.A. Smith, R.G. Goodwin, K.E. Stremler, V.P. Fung, H. Madani, and M.B. Widmer, *Soluble tumor necrosis factor(TNF) receptors are effective therapeutic agents in lethal endotoxemia and function simultaneously as both TNF carriers and TNF antagonists.* J Immunol, 1993. 151(3): p. 1548-61.

Murata, Y., U. Nannmark, B. Rydevik, K. Takahashi, and K. Olmarker, *Nucleus pulposus-induced apoptosis in dorsal root ganglion following experimental disc herniation in rats.* Spine, 2006. 31(4): p. 382-90.

Murata, Y., U. Nannmark, B. Rydevik, K. Takahashi, and K. Olmarker, *The role of tumor necrosis factor-alpha in apoptosis of dorsal root ganglion cells induced by herniated nucleus pulposus in rats.* Spine, 2008. 33(2): p. 155-62.

Murata, Y., K. Olmarker, K. Larsson, K. Takahashi, and B. Rydevik, *Production of tumor necrosis factor-alpha from porcine nucleus pulposus cells at various time points in cell culture under conditions of nutritional deficiency.* Cytokine, 2006. 34(3-4): p. 206-11.

Murata, Y., A. Onda, B. Rydevik, I. Takahashi, K. Takahashi, and K. Olmarker, *Changes in pain behavior and histologic changes caused by application of tumor necrosis factor-alpha to the dorsal root ganglion in rats.* Spine, 2006. 31(5): p. 530-5.

Murata, Y., A. Onda, B. Rydevik, K. Takahashi, and K. Olmarker, *Selective inhibition of tumor necrosis factor-alpha prevents nucleus pulposus-induced histologic changes in the dorsal root ganglion.* Spine, 2004. 29(22): p. 2477-84.

Murata, Y., A. Onda, B. Rydevik, K. Takahashi, and K. Olmarker, *Distribution and appearance of tumor necrosis factor-alpha in the dorsal root ganglion exposed to experimental disc herniation in rats.* Spine, 2004. 29(20): p. 2235-41.

Nawashiro, H., D. Martin, and J.M. Hallenbeck, *Neuroprotective effects of TNF binding protein in focal cerebral ischemia.* Brain Res, 1997. 778(2): p. 265-71.

Nedjai, B. et al., *Proinflammatory Action of the Antiinflammatory Drug Infliximab in Tumor Necrosis Factor Receptor—Associated Periodic Syndrome.* Arthritis & Rheumatism, vol. 60, No. 2, 2009, pp. 619-625.

Olmarker, K., *Radicular pain—recent pathophysiologic concepts and therapeutic implications.* Schmerz, 2001. 15(6): p. 425-9.

Olmarker, K., G. Byrod, M. Cornefjord, C. Nordborg, and B. Rydevik, *Effects of methylprednisolone on nucleus pulposus-induced nerve root injury.* Spine, 1994. 19(16): p. 1803-8.

Olmarker, K. and K. Larsson, *Tumor necrosis factor alpha and nucleus-pulposus-induced nerve root injury.* Spine, 1998. 23(23): p. 2538-44.

Olmarker, K., M. Nutu, and R. Storkson, *Changes in spontaneous behavior in rats exposed to experimental disc herniation are blocked by selective TNF-alpha inhibition.* Spine, 2003. 28(15): p. 1635-41; discussion 1642.

Olmarker, K. And B. Rydevik, *Selective inhibition of tumor necrosis factor-alpha prevents nucleus pulposus-induced thrombus formation, intraneural edema, and reduction of nerve conduction velocity: possible implications for future pharmacologic treatment strategies of sciatica.* Spine, 2001. 26(8): p. 863-9.

Onda, A., Y. Murata, B. Rydevik, K. Larsson, S. Kikuchi, and K. Olmarker, *Infliximab attenuates immunoreactivity of brain-derived neurotrophic factor in a rat model of herniated nucleus pulposus.* Spine, 2004. 29(17): p. 1857-61.

Pardridge, W.M., *The blood-brain barrier: bottleneck in brain drug development.* NeuroRx, 2005. 2(1): p. 3-14.

Perry, R.T., J.S. Collins, H. Wiener, R. Acton, and R.C. Go, *The role of TNF and its receptors in Alzheimer's disease.* Neurobiol Aging, 2001. 22(6): p. 873-83.

Pickering, M., D. Cumiskey, and J.J. O'Connor, *Actions of TNF-alpha on glutamatergic synaptic transmission in the central nervous system.* Exp Physiol, 2005. 90(5): p. 663-70.

Ramos, E.M., M.T. Lin, E.B. Larson, I. Maezawa, L.H. Tseng, K.L. Edwards, G.D. Schellenberg, J.A. Hansen, W.A. Kukull, and L.W. Jin, *Tumor necrosis factor alpha and interleukin 10 promoter region polymorphisms and risk of late-onset Alzheimer disease.* Arch Neurol, 2006. 63(8): p. 1165-9.

Rutgeerts, P., L. Lemmens, G. Van Assche, M. Noman, I. Borghini-Fuhrer, and R. Goedkoop, *Treatment of active Crohn's disease with onercept(recombinant human soluble p55 tumour necrosis factor receptor): results of a randomized, open-label, pilot study.* Aliment Pharmacol Ther, 2003. 17(2): p. 185-92.

Saha, R.N., X. Liu, and K. Pahan, *Up-regulation of BDNF in astrocytes by TNF-alpha: a case for the neuroprotective role of cytokine.* J Neuroimmune Pharmacol, 2006. 1(3): p. 212-22.

San Millan Ruiz, D., P. Gailloud, D.A. Rufenacht, J. Delavelle, F. Henry, and J.H. Fasel, *The craniocervical venous system in relation to cerebral venous drainage.* AJNR Am J Neuroradiol, 2002. 23(9): p. 1500-8.

Scallon, B.J. et al., *Functional comparisons of different tumor necrosis factor receptor/IgG fusion proteins.* Cytokine, vol. 7, No. 8 (Nov.), 1995: pp. 759-770.

Scallon, B., Cai, A. et al., *Binding and Functional Comparisons of Two Types of Tumor Necrosis Factor Antagonists.* Pharmacol Exp Ther, 2002. 301(2): p. 418-26.

Sharma, H.S., T. Winkler, E. Stalberg, T. Gordh, P. Alm, and J. Westman, *Topical application of TNF-alpha antiserum attenuates spinal cord trauma induced edema formation, microvascular permeability disturbances and cell injury in the rat.* Acta Neurochir Suppl, 2003. 86: p. 407-13.

Sheng, J.G., S.H. Bora, G. Xu, D.R. Borchelt, D.L. Price, and V.E. Koliatsos, *Lipopolysaccharide-induced-neuroinflammation increases intracellular accumulation of amyloid precursor protein and amyloid beta peptide in APPswe transgenic mice.* Neurobiol Dis, 2003. 14(1): p. 133-45.

Shinpo, K., S. Kikuchi, F. Moriwaka, and K. Tashiro, *Protective effects of the TNF-ceramide pathway against glutamate neurotoxicity on cultured mesencephalic neurons.* Brain Res, 1999. 819(1-2): p. 170-3.

Shohami, E., R. Gallily, R. Mechoulam, R. Bass, and T. Ben-Hur, *Cytokine production in the brain following closed head injury: dexanabinol(HU-211) is a novel TNF-alpha inhibitor and an effective neuroprotectant.* J Neuroimmunol, 1997. 72(2): p. 169-77.

Shubayev, V.I. and R.R. Myers, *Upregulation and interaction of TNFalpha and gelatinases A and B in painful peripheral nerve injury.* Brain Res, 2000. 855(1): p. 83-9.

Shubayev, V.I. and R.R. Myers, *Axonal transport of TNF-alpha in painful neuropathy: distribution of ligand tracer and TNF receptors.* J Neuroimmunol, 2001. 114(1-2): p. 48-56.

Shubayev, V.I. and R.R. Myers, *Anterograde TNF alpha transport from rat dorsal root ganglion to spinal cord and injured sciatic nerve.* Neurosci Lett, 2002. 320(1-2): p. 99-101.

Shubayev, V.I. and R.R. Myers, *Endoneurial remodeling by TNFalph- and TNFalpha-releasing proteases. A spatial and temporal co-localization study in painful neuropathy.* J Peripher Nerv Syst, 2002. 7(1): p. 28-36.

Sicotte, N.L. and R.R. Voskuhl, *Onset of multiple sclerosis associated with anti-TNF therapy.* Neurology, 2001. 57(10): p. 1885-8.

Sjogren, M., S. Folkesson, K. Blennow, and E. Tarkowski, *Increased intrathecal inflammatory activity in frontotemporal dementia: pathophysiological implications.* J Neurol Neurosurg Psychiatry, 2004. 75(8): p. 1107-11.

Sommer, C., M. Schafers, M. Marziniak, and K.V. Toyka, *Etanercept reduces hyperalgesia in experimental painful neuropathy.* J Peripher Nerv Syst, 2001. 6(2): p. 67-72.

Spuler, S., T. Yousry, A. Scheller, R. Voltz, E. Holler, M. Hartmann, M. Wick, and R. Hohlfeld, *Multiple sclerosis: prospective analysis of TNF-alpha and 55 kDa TNF receptor in CSF and serum in correlation with clinical and MRI activity.* J Neuroimmunol, 1996. 66(1-2): p. 57-64.

Suzuki, T., I. Hide, K. Ido, S. Kohsaka, K. Inoue, and Y. Nakata, *Production and release of neuroprotective tumor necrosis factor by P2X7 receptor-activated microglia.* J Neurosci, 2004. 24(1): p. 1-7.

Tariot, P.N. and H.J. Federoff, *Current treatment for Alzheimer disease and future prospects.* Alzheimer Dis Assoc Disord, 2003. 17 Suppl 4: p. S105-13.

Tarkowski, E., *Cytokines in dementias.* Curr Drug Targets Inflamm Allergy, 2002. 1(2): p. 193-200.

Tarkowski, E., N. Andreasen, A. Tarkowski, and K. Blennow, *Intrathecal inflammation precedes development of Alzheimer's disease.* J Neurol Neurosurg Psychiatry, 2003. 74(9): p. 1200-5.

Tarkowski, E., K. Blennow, A. Wallin, and A. Tarkowski, *Intracerebral production of tumor necrosis factor-alpha, a local neuroprotective agent, in Alzheimer disease and vascular dementia.* J Clin Immunol, 1999. 19(4): p. 223-30.

Tarkowski, E., A.M. Liljeroth, L. Minthon, A. Tarkowski, A. Wallin, and K. Blennow, *Cerebral pattern of pro- and anti-inflammatory cytokines in dementias.* Brain Res Bull, 2003. 61(3): p. 255-60.

Tartaglia, L.A., R.F. Weber, I.S. Figari, C. Reynolds, M.A. Palladino, Jr., and D.V. Goeddel, *The two different receptors for tumor necrosis factor mediate distinct cellular responses.* Proc Natl Acad Sci U S A, 1991. 88(20): p. 9292-6.

Tedde, A., A.L. Putignano, B. Nacmias, S. Bagnoli, E. Cellini, and S. Sorbi, *Lack of association between TNF-alpha polymorphisms and Alzheimer's disease in an Italian cohort.* Neurosci Lett, 2008.

Terrado, J., D. Monnier, D. Perrelet, D. Vesin, S. Jemelin, W.A. Buurman, L. Mattenberger, B. King, A.C. Kato, and I. Garcia, *Soluble TNF receptors partially protect injured motoneurons in the postnatal CNS.* Eur J Neurosci, 2000. 12(9): p. 3443-7.

Tobinick, E., *TNF-alpha inhibition for potential therapeutic modulation of SARS coronavirus infection.* Curr Med Res Opin, 2004. 20(1): p. 39-40.

Tobinick, E., *Spinal delivery of p38: TNF-alpha inhibitors.* PLoS Med, 2006. 3(11): p. e511.

Tobinick, E., *Perispinal etanercept for treatment of Alzheimer's disease.* Curr Alzheimer Res, 2007. 4(5): p. 550-2.

Tobinick, E., *Perispinal etanercept for neuroinflammatory disorders.* Drug Discov Today, 2008.

Tobinick, E., *Perispinal etanercept produces rapid improvement in primary progressive aphasia: identification of a novel, rapidly reversible TNF-mediated pathophysiologic mechanism.* Medscape J Med, 2008. 10(6): p. 135.

Tobinick, E. and S. Davoodifar, *Efficacy of etanercept delivered by perispinal administration for chronic back and/or neck disc-related pain: a study of clinical observations in 143 patients.* Curr Med Res Opin, 2004. 20(7): p. 1075-85.

Tobinick, E., H. Gross, A. Weinberger, and H. Cohen, *TNF-alpha modulation for treatment of Alzheimer's disease: a 6-month pilot study.* MedGenMed, 2006. 8(2): p. 25.

Tobinick, E. and C.P. Vega, *The cerebrospinal venous system: anatomy, physiology, and clinical implications.* MedGenMed, 2006. 8(1): p. 53.

Tobinick, E.L., *Targeted etanercept for treatment-refractory pain due to bone metastasis: two case reports*. Clin Ther, 2003. 25(8): p. 2279-88.

Tobinick, E.L., *Targeted etanercept for discogenic neck pain: uncontrolled, open-label results in two adults*. Clin Ther, 2003. 25(4): p. 1211-8.

Tobinick, E.L., *Re: Inflammatory markers and the risk of Alzheimer disease: the Framingham Study*. Neurology, 2008. 70(14): p. 1222-3; author reply 1223.

Tobinick, E.L., *A critique of intradiscal administration for treatment of radiculopathy*. Anesthesiology, 2008. 108(2): p. 334; author reply 335.

Tobinick, E.L. and S. Britschgi-Davoodifar, *Perispinal TNF-alpha inhibition for discogenic pain*. Swiss Med Wkly, 2003. 133(11-12): p. 170-7.

Tobinick, E.L. and H. Gross, *Rapid improvement in verbal fluency and aphasia following perispinal etanercept in Alzheimer's disease*. BMC Neurol, 2008. 8: p. 27.

Tobinick, E.L. and H. Gross, *Rapid cognitive improvement in Alzheimer's disease following perispinal etanercept administration*. J Neuroinflammation, 2008. 5: p. 2.

Tracey, D. et al. *Tumor necrosis factor antagonist mechanisms of action: A comprehensive review*. Pharmacology & Therapeutics 117 (2008) pp. 244-279.

Tracey, K.J. and Cerami, A. *Tumor necrosis factor: An updated review of its biology*. Critical Care Medicine, vol. 21, No. 10, pp. S415-S422, 1993.

Turrin, N.P. and S. Rivest, *Tumor necrosis factor alpha but not interleukin 1 beta mediates neuroprotection in response to acute nitric oxide excitotoxicity*. J Neurosci, 2006. 26(1): p. 143-51.

van Oosten, B.W., F. Barkhof, L. Truyen, J.B. Boringa, F.W. Bertelsmann, B.M. von Blomberg, J.N. Woody, H.P. Hartung, and C.H. Polman, *Increased MRI activity and immune activation in two multiple sclerosis patients treated with the monoclonal anti-tumor necrosis factor antibody cA2*. Neurology, 1996. 47(6): p. 1531-4.

Vima, S., M. Deckert, S. Lutjen, S. Soltek, K.E. Foulds, H. Shen, H. Korner, J.D. Sedgwick, and D. Schluter, *TNF is important for pathogen control and limits brain damage in murine cerebral listeriosis*. J Immunol, 2006. 177(6): p. 3972-82.

Wagner, R. and R.R. Myers, *Endoneurial injection of TNF-alpha produces neuropathic pain behaviors*. Neuroreport, 1996. 7(18): p. 2897-901.

Wen, T.S., D.C. Randall, and J.F. Zolman, *Protein accumulation in cerebrospinal fluid during -90 degrees head-down tilt in rabbit*. J Appl Physiol, 1994. 77(3): p. 1081-6.

Wiendl, H. and R. Hohlfeld, *Therapeutic approaches in multiple sclerosis: lessons from failed and interrupted treatment trials*. BioDrugs, 2002. 16(3): p. 183-200.

Wilson, C.J., C.E. Finch, and H.J. Cohen, *Cytokines and cognition—the case for a head-to-toe inflammatory paradigm*. J Am Geriatr Soc, 2002. 50(12): p. 2041-56.

Carlson, N.G, Whitney A. Wieggel, Jian Chen, Annalisa Bacchi, Scott W. Rogers, and Lorise C. Gahring, Inflammatory Cytokines IL-1a, IL-lb, IL-6, and TNF-a Impart Neuroprotection to an Excitotoxin Through Distinct Pathways. The Journal of Immunology, 1999, 163: 3963-3968.

Looseley A. Corning and Cocaine: the Advent of Spinal Anaesthesia. *Grand Rounds in Exp-Med*, 9, L1-L4 (2009), DOI:10.1102/1470-5206.2009.L001.

Calthorpe N. Development of the Cutting Spinal Needle TipThe history of spinal needles: getting to the point. *Anaesthesia*, 59, 1231-1241 (2004).

Gerancher JC. Combined Spinal-Epidural Techniques in Obstetrics. *Techniques in Regional Anesthesia and Pain Management*, 2(4), 1 79-187 (1998).

Cousins MJ, Bridenbaugh PO, *Spinal Anesthesia, Chapter 1(p. 11; History of Neural Blockade and Pain Management,)* in Neural Blockade in Clinical Anesthesia and Management of Pain (Lippencott-Raven, New York, 1998).

Harger JR, Christofferson EA, Stokes AJ. Peridural Anesthesia: A Consideration of 1000 Cases. *American Journal of Surgery*, 52(1), 24-31 (1941).

Corning JL. A Further Contribution on Local Medication of the Spinal Cord, with cases *Transactions of the Medical Society of the Sate of New York*, 260-269 (1888).

Corning JL. *Spinal Anaesthesia and Local Medication of the Cord*, Chapter 11 in Local Anaesthesia in General Medicine and Surgery (D. Appleton and Company, New York, 1886).

Pardridge, W.M, *The Blood-Brain Barrier: Bottleneck in Brain Drug Development*, The Journal of the American Society for Experimental NeuroTherapeutics vol. 2, 3-14, Jan. 2005.

Duale et al., *Epidural versus intrathecal morphine for postoperative analgesia after Caesarean section*, British Journal of Anesthesia 91 (5): 690-4 (2003).

Gourlay et al., *Cephalad Migration of Morphine in CSF Following Lumbar Epidural Administration in Patients with Cancer Pain*, Pain, 23 (1985) 317-326.

Nordberg et al., Anesthesiology, 58, 545-551, 1983; Max et al., Clin Pharmacol Ther 38:631-641, 1985.

Max, et al., *Epidural and intrathecal opiates: Cerebrospinal fluid and plasma profiles in patients with chronic cancer pain* Clin Pharmacol Ther 38:631-641, 1985.

Plancarte et al., Current Opinion in Anesthesiology 1994, 7:444-447.

* cited by examiner

CYTOKINE ANTAGONISTS FOR NEUROLOGICAL AND NEUROPSYCHIATRIC DISORDERS

RELATED APPLICATIONS

This application is a divisional of U.S. application Ser. No. 10/269,745, filed on Oct. 9, 2002, now U.S. Pat. No. 6,982,089, which is a continuation-in-part of application Ser. No. 10/236,097, filed on Sep. 6, 2002, now abandoned, which is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of Ser. No. 09/666,068, filed Dec. 11, 2000, now U.S. Pat. No. 6,379,666, which is a divisional of application Ser. No. 09/476,643, filed on Dec. 31, 1999, now U.S. Pat. No. 6,177,077, which is a continuation-in-part of application Ser. No. 09/275,070, filed on Mar. 23, 1999, now U.S. Pat. No. 6,015,557, which is a continuation-in-part of application Ser. No. 09/256,388, filed on Feb. 24, 1999, now abandoned.

FIELD OF THE INVENTION

The present invention relates to novel methods of use of specific cytokine antagonists for the treatment of neuropsychiatric and neurological disorders in humans. More particularly, these cytokine antagonists are used in a new treatment of neuropsychiatric and neurologic diseases and disorders, including, but not limited to affective disorders, including unipolar and bipolar affective disorders; schizoaffective illness, schizophrenia, autism, depression, anorexia nervosa, obsessive-compulsive disorders, narcotic addiction, and smoking cessation/nicotine withdrawal; diseases and disorders of the brain; neurodegenerative disorders, including but not limited to Parkinson's Disease and Alzheimer's Disease; spinal cord injury, amyotrophic lateral sclerosis; headache syndromes, including, but not limited to migraine headaches and cluster headaches; neurologic disorders associated with neuropathic pain, including, but not limited to lumbar and cervical radiculopathy, low back pain, vertebral disc disease, fibromyalgia, post-herpetic neuralgia, and reflex sympathetic dystrophy; and chronic fatigue syndrome; utilizing specific anatomic methods of administration of these specific biologics. The delivery of these cytokine antagonists is performed by specific methods, most of which fall into the categories of perispinal administration or intranasal administration. Perispinal administration involves an anatomically localized injection performed so as to deliver the therapeutic molecule directly into the vicinity of the spine. Perispinal administration includes, but is not limited to the subcutaneous, intramuscular, interspinous, epidural, peridural, parenteral, or intrathecal routes, and may be perilesional or alternatively, particularly when treating diseases of the brain, remote from the ultimate site of pathology. Intranasal administration includes the delivery of these particular cytokine antagonists by instillation into the nasal passages, either by nasal spray or nasal inhaler. The cytokine antagonists of consideration are those designed to block the action of, inhibit, or antagonize the biologic effects of tumor necrosis factor-alpha (TNF) or interleukin-1 (IL-1). These antagonists may take the form of a fusion protein (such as etanercept); a monoclonal antibody (such as infliximab); a binding protein (such as onercept, Serono); an antibody fragment (such as CDP 870, Pharmacia); or other types of molecules which are potent, selective, and specific inhibitors of the action of these pro-inflammatory cytokines and are capable of being used by parenteral injection.

BACKGROUND OF THE INVENTION

Localized administration for the treatment of localized clinical disorders has many clinical advantages over the use of conventional systemic treatment. Locally administered medication after delivery diffuses through local capillary, venous, arterial, and lymphatic action to reach the anatomic site of pathology, or, alternatively, to reach the cerebrospinal fluid (CSF). In addition local administration of a biologic in the vicinity of the spine (perispinal administration) has the key advantage of improved delivery of the agent to the central nervous system (CNS). Local intranasal administration of a biologic is another method to improve delivery of the biologic to the CNS, and is discussed here as a method to treat neuropsychiatric disorders, including disorders of mood (depression, bipolar disorder) utilizing TNF antagonists or IL-1 antagonists.

All of the cytokine antagonists which are currently available have been developed for systemic administration. This is because all were developed to treat systemic illnesses, including rheumatoid arthritis, juvenile rheumatoid arthritis, psoriatic arthritis, or Crohn's Disease.

The use of cytokine antagonists to treat neurological disorders is discussed in several previous patents of this inventor, including U.S. Pat. Nos. 6,015,557, 6,177,077, 6,419,944 B2 and other pending applications of this inventor. This invention includes further applications of these ideas.

Perispinal administration of biologics when compared to systemic administration, carries with it one or more of the following advantages:

1) greater efficacy due to the achievement of higher local concentration;
2) greater efficacy due to the ability of the administered therapeutic molecule to reach the target tissue without degradation caused by hepatic or systemic circulation;
3) more rapid onset of action;
4) longer duration of action;
5) Potentially fewer side effects, due to lower required dosage;
6) greatly improved efficacy due to improved delivery of the therapeutic molecule to the CNS.

Clinical experience utilizing perispinal administration of etanercept for treating lumbar and cervical radiculopathy and other forms of neuropathic pain caused by vertebral disc disease has demonstrated the dramatic efficacy, and the extraordinarily rapid onset of action produced by perispinal administration of etanercept for these disorders. Perispinal administration of the other cytokine antagonists of consideration here, for treating other neurological disorders or for treating neuropsychiatric disorders, as partially enumerated above, shares the above advantages.

The therapeutic molecules of consideration here have many biologic effects. Etanercept, for example, in addition to being a potent anti-inflammatory also has important anti-apoptotic effects which may be of particular importance in treating neurodegenerative diseases, such as Alzheimer's Disease and Parkinson's Disease, where apoptosis plays a pathogenetic role.

Biologics have been developed which have been shown to offer dramatic clinical benefit for systemic illnesses in humans, even for those disorders which have not responded to large and repeated doses of corticosteroids. These biologics fall into the category of cytokine antagonists because they block, or antagonize, the biologic action of a specific cytokine which has adverse clinical effects. These cytokines include the pro-inflammatory cytokines interleukin-1 and TNF. For the purposes of this discussion, "antagonist", "inhibitor", and "blocker" are used interchangeably.

Specific inhibitors of TNF, only recently commercially available, now provide for therapeutic intervention in TNF mediated disorders. These agents have been developed to treat systemic illnesses, and therefore have been developed for systemic administration. Various biopharmaceutical companies have developed TNF antagonists to treat systemic illnesses: Immunex Corporation developed etanercept (Enbrel) to treat rheumatoid arthritis; Johnson and Johnson developed infliximab (Remicade) to treat Crohn's Disease and rheumatoid arthritis; D2E7, a human anti-TNF monoclonal antibody (Abbott) is being developed to treat rheumatoid arthritis and Crohn's Disease; Celltech is developing CDP 571 to treat Crohn's Disease and CDP 870 to treat rheumatoid arthritis; and Serono is developing onercept, a recombinant TNF binding protein (r-TBP-1) for treating rheumatoid arthritis and psoriasis/psoriatic arthritis.

Recent research has demonstrated that a new TNF antagonist can be manufactured from an existing molecule by subtracting a portion of the amino acid sequence from the molecule. This has the advantage of making the molecule smaller. This smaller molecule can be easier to manufacture and may have clinical advantages, such as reduced immunogenicity in the human in vivo. Therefore, the molecules of consideration here shall also include, in addition to those specified, any molecule which contains a fragment of any of the named molecules. A fragment shall be defined as an identical amino acid sequence 50% or greater in length of the original molecule and possessing TNF binding capability or interleukin-1 binding capability.

DESCRIPTION OF THE PRIOR ART

Pharmacologic chemical substances, compounds and agents which are used for the treatment of neurological disorders, trauma, injuries and compression having various organic structures and metabolic functions have been disclosed in the prior art. For example, U.S. Pat. Nos. 5,756,482 and 5,574,022 to ROBERTS et al disclose methods of attenuating physical damage to the nervous system and to the spinal cord after injury using steroid hormones or steroid precursors such as pregnenolone, and pregnenolone sulfate in conjunction with a non-steroidal anti-inflammatory substance such as indomethacin. These prior art patents do not teach the use of specific cytokine antagonists administered by the perispinal route as a way of treating neurological or neuropsychiatric disorders or diseases, as in the present invention.

U.S. Pat. No. 5,863,769 discloses using IL-1 RA for treating various diseases. However, it does not disclose administering cytokine antagonists by the perispinal route as a way of treating neurological or neuropsychiatric disorders or diseases.

U.S. Pat. No. 6,013,253 discloses using interferon and IL-1 RA for treating multiple sclerosis. However, it does not disclose administering cytokine antagonists by the perispinal route as a way of treating neurological or neuropsychiatric disorders or diseases.

U.S. Pat. No. 5,075,222 discloses the use of IL-1 inhibitors for treatment of various disorders. However, it does not disclose administering cytokine antagonists by the perispinal route as a way of treating neurological or neuropsychiatric disorders or diseases.

U.S. Pat. No. 6,159,460 discloses the use of IL-1 inhibitors for treatment of various disorders. However, it does not disclose administering cytokine antagonists by the perispinal route as a way of treating neurological or neuropsychiatric disorders or diseases.

U.S. Pat. No. 6,096,728 discloses the use of IL-1 inhibitors for treatment of various disorders. However, it does not disclose administering cytokine antagonists by the perispinal route as a way of treating neurological or neuropsychiatric disorders or diseases.

U.S. Pat. No. 6,277,969 discloses the use of anti-TNF antibodies for treatment of various disorders. However, it does not disclose administering cytokine antagonists by the perispinal route as a way of treating neurological or neuropsychiatric disorders or diseases.

U.S. Pat. No. 5,605,690 discloses the use of TNF inhibitors for treatment of various disorders. However, it does not disclose administering cytokine antagonists by the perispinal route as a way of treating neurological or neuropsychiatric disorders or diseases.

None of the prior art patents disclose or teach the use of localized administration of a cytokine antagonist as in the present invention as a way of treating neurological or neuropsychiatric disorders or diseases, in which the cytokine antagonist provides the patient with a better opportunity to heal, slows disease progression, or otherwise improves the patient's health.

Accordingly, it is an object of the present invention to provide a biologic administered through perispinal administration as a new method of pharmacologic treatment of neurological or neuropsychiatric diseases or disorders such that the use of these biologics will result in the amelioration of these conditions.

Another object of the present invention is to provide cytokine antagonists for providing suppression and inhibition of the action of specific cytokines in a human to treat neurological or neuropsychiatric diseases or disorders.

Another object of the present invention is to provide cytokine antagonists that produce biologic effects in patients with neurological or neuropsychiatric diseases or disorders by inhibiting the action of specific cytokines in the human body for the immediate, short term (acute conditions) and long term (chronic conditions), such that these biologic effects will produce clinical improvement in the patient and will give the patient a better opportunity to heal, improve cognitive function, slow disease progression, prevent neurological damage, reduce pain, or otherwise improve the patient's health.

Another object of the present invention is to provide cytokine antagonists, using anatomically localized administration in the vicinity of the spine as the preferred forms of administration, that provide therapeutic benefit utilizing either acute or chronic treatment regimens for treating neurological or neuropsychiatric diseases or disorders.

SUMMARY OF THE INVENTION

The present invention provides methods for treating neurological or neuropsychiatric diseases or disorders in humans by administering to the human a therapeutically effective dose of a specific biologic. The biologics of consideration include antagonists of tumor necrosis factor-alpha or of interleukin-1. The administration of these biologics is performed by specific methods, most, but not all of which fall into the categories of anatomically localized administration involving perispinal or intranasal delivery. Anatomically localized administration involving perispinal use includes, but is not limited to the subcutaneous, intramuscular, interspinous, epidural, peridural, parenteral or intrathecal routes.

DETAILED DESCRIPTION OF THE PREFERRED EMBODIMENTS

Perispinal administration is a novel new concept for a delivery method for cytokine antagonists for treating neurological or neuropsychiatric diseases.

For the purposes of this discussion, "perispinal" means in the anatomic vicinity of the spine. For this discussion "anatomic vicinity" is generally defined as within 10 centimeters, or functionally defined as in close enough anatomic proximity to allow the therapeutic molecules of consideration herein to reach the spine and/or the subarachnoid space surrounding the spinal cord in therapeutic concentration when administered directly to this area. For the treatment of brain disorders, such as Alzheimer's, perispinal administration is effective because it delivers the biologic to the CNS in a therapeutic amount. This is accomplished through enhanced delivery of the therapeutic molecule to the CNS, either by direct diffusion or via enhanced delivery into the cerebrospinal fluid (CSF) which is present in the thecal sac. This usually occurs without direct intrathecal injection, but rather by diffusion from the peridural space into the subarachnoid space. Direct injection of these specific cytokine antagonists into the CSF (intrathecal administration) is also a form of localized anatomic administration and can be accomplished by the perispinal route.

One of the advantages of perispinal delivery is that administration is simplified. For example, administration for the treatment of an annular tear of an intervertebral disc in the lumbar spine is effective by the interspinous route adjacent to the involved disc. This route is simple and safe. Hemorrhage due to the use of long or large bore needles is minimized because perispinal administration, by the subcutaneous route, requires only a short, narrow bore needle. Time-consuming and difficult epidural injection is not necessary. Epidural administration, for the purposes of this patent, is also a form of perispinal administration, and, in certain clinical circumstances may be the delivery method of choice, despite its greater difficulty and greater risk. Local perispinal administration also has the advantage of providing a depot of therapeutic medication in the surrounding tissue, which will provide therapeutic levels of medication to the treatment site for a prolonged period of time. This decreases the necessity for another injection of medication. Additionally, administering medication locally limits the exposure of the medication to the systemic circulation, thereby decreasing renal and hepatic elimination of the medication, and decreasing exposure of the medication to systemic metabolism. All of these factors tend to increase the therapeutic half-life of the administered cytokine antagonist. Intranasal administration is also a form of localized anatomic administration. It shares the above advantages with perispinal administration, and has the additional advantage of delivering the biologic to the area (upper nasal passages) directly adjacent to the brain. Additionally the biologics are delivered in this same manner directly to branches of the olfactory nerve, providing another route of delivery to the CNS. Taken together, all of these forms of localized anatomic administration have significant clinical advantages over the various forms of systemic administration previously used to deliver these cytokine antagonists. These forms of systemic administration include the intravenous route; the intramuscular route, when the site of intramuscular administration is remote from the site of pathology; the subcutaneous route, when the site of subcutaneous administration is remote from the site of pathology (such as an abdominal, thigh, or arm administration for the treatment of sciatica); or other methods of administration which rely on the use of the systemic circulation to deliver the medication to the target area of pathology.

For the sake of this invention, the following definitions also apply: perilesional is defined as in anatomic proximity to the site of the pathologic process being treated; and peridural is defined as in anatomic proximity to the dura of the spinal cord. The "interspinous route" for the purposes of this patent, is defined as parenteral injection through the skin in the midline, in the interspace between two spinous processes, to deliver the therapeutic molecule in anatomic proximity to the spine.

Biologics to be used for the purposes of this patent fall into the general categories of TNF antagonists or interleukin-1 antagonists.

TNF antagonists include, but are not limited to the following: etanercept (Enbrel®-Amgen); infliximab (Remicade®-Johnson and Johnson); D2E7, a human anti-TNF monoclonal antibody (Knoll Pharmaceuticals, Abbott Laboratories); CDP 571 (a humanized anti-TNF IgG4 antibody); CDP 870 (an anti-TNF alpha humanized monoclonal antibody fragment), both from Celltech; soluble TNF receptor Type I (Amgen); pegylated soluble TNF receptor Type I (PEGs TNF-R 1) (Amgen); and onercept, a recombinant TNF binding protein (r-TBP-1) (Serono). Antagonists of interleukin-1 include, but are not limited to Kineret® (recombinant IL1-RA, Amgen), IL1-Receptor Type 2 (Amgen) and IL-1 Trap (Regeneron).

In one preferred embodiment a patient with bipolar affective disorder complaining of severe depression is treated by injection of a TNF antagonist selected from the group of etanercept, infliximab, CDP 870, D2E7, or onercept in a therapeutically effective dose to the anatomic area adjacent to the spine.

In one preferred embodiment a patient with Alzheimer's Disease with dementia is treated by injection of a TNF antagonist selected from the group of etanercept, infliximab, CDP 870, D2E7, or onercept in a therapeutically effective dose to the anatomic area adjacent to the spine, with the dose repeated as a form of chronic therapy at intervals as often as twice per week to as little as once per three months.

In one preferred embodiment a patient with post-herpetic neuralgia complaining of severe persistent pain is treated by injection of a TNF antagonist selected from the group of etanercept, infliximab, CDP 870, D2E7, or onercept in a therapeutically effective dose to the anatomic area adjacent to the spine with a single dose administered 48 hours after beginning a course of antiviral medication.

In another preferred embodiment a patient with clinical depression is treated by intranasal administration of a TNF antagonist selected from the group of etanercept, infliximab, CDP 870, D2E7, or onercept in a therapeutically effective dose.

In another preferred embodiment a patient with lumbar radiculopathy due to an intervertebral disc herniation is treated by injection of a IL-1 antagonist selected from the group of IL-1 RA, Kineret, IL-1 R type 2 or IL-1 Trap in a therapeutically effective dose to the anatomic area adjacent to the involved disc.

In another preferred embodiment injection of the therapeutic molecule to the anatomic area adjacent to the spine is accomplished by interspinous injection.

In another preferred embodiment interspinous injection is accomplished by injection through the skin in the anatomic area between two adjacent spinous processes of the vertebral column.

An example of one preferred embodiment for treatment of lumbar radiculopathy due to disc herniation at the L 3-4 interspace is the perispinal administration of etanercept 25 mg by injecting through the skin of the back, between the L3 and L4 spinous processes, to deliver etanercept in anatomic proximity to the site of disc herniation.

In another preferred embodiment injection of the therapeutic molecule to the anatomic area adjacent to the disc herniation is accomplished by subcutaneous injection.

In another preferred embodiment injection of the therapeutic molecule to the anatomic area adjacent to the disc herniation is accomplished by epidural injection.

In another preferred embodiment injection of the therapeutic molecule to the anatomic area adjacent to the disc herniation is accomplished by peridural injection.

In another preferred embodiment injection of the therapeutic molecule to the anatomic area adjacent to the disc herniation is accomplished by perispinal injection.

Scientific Background:

Antibodies (immunoglobulins) are proteins produced by one class of lymphocytes (B cells) in response to specific exogenous foreign molecules (antigens). Monoclonal antibodies (mAB), identical immunoglobulin copies which recognize a single antigen, are derived from clones (identical copies) of a single B cell. This technology enables large quantities of an immunoglobulin with a specific target to be mass produced.

Monoclonal antibodies with a high affinity for a specific cytokine will tend to reduce the biologic activity of that cytokine. Substances which reduce the biologic effect of a cytokine can be described in any of the following ways: as a cytokine blocker; as a cytokine inhibitor; or as a cytokine antagonist. In this patent, the terms blocker, inhibitor, and antagonist are used interchangeably with respect to cytokines.

Advances in biotechnology have resulted in improved molecules as compared to simply using monoclonal antibodies. One such molecule is CDP 870 which, rather than being a monoclonal antibody, is a new type of molecule, that being an antibody fragment. By removing part of the antibody structure, the function of this molecule is changed so that it acts differently in the human body. Another new type of molecule, distinct from monoclonal antibodies and soluble receptors, is a fusion protein. One such example is etanercept. This molecule has a distinct function which acts differently in the human body than a simple soluble receptor or receptors.

Monoclonal antibodies, fusion proteins, and all of the specific molecules discussed above under the categories of TNF antagonists and interleukin antagonists are considered biologics, in contrast to drugs that are chemically synthesized. These biologics are derived from living sources (such as mammals (including humans), other animals, and microorganisms). The biologics mentioned above are manufactured using biotechnology, which usually involves the use of recombinant DNA technology. Cytokine antagonists are one type of biologic. Biologics are regulated through a specific division of the FDA.

Cytokine antagonists can take several forms. They may be monoclonal antibodies (defined above). They may be a monoclonal antibody fragment. They may take the form of a soluble receptor to that cytokine. Soluble receptors freely circulate in the body. When they encounter their target cytokine they bind to it, effectively inactivating the cytokine, since the cytokine is then no longer able to bind with its biologic target in the body. An even more potent antagonist consists of two soluble receptors fused together to a specific portion of an immunoglobulin molecule (Fc fragment). This produces a dimer composed of two soluble receptors which have a high affinity for the target, and a prolonged half-life. This new molecule is called a fusion protein. An example of this new type of molecule, called a fusion protein, is etanercept (Enbrel).

Tumor necrosis factor (TNF), a naturally occurring cytokine present in humans and other mammals, plays a key role in the inflammatory response, in the immune response and in the response to infection. TNF is formed by the cleavage of a precursor transmembrane protein, forming soluble molecules which aggregate in vivo to form trimolecular complexes. These complexes then bind to receptors found on a variety of cells. Binding produces an array of pro-inflammatory effects, including release of other pro-inflammatory cytokines, including IL-6, IL-8, and IL-1; release of matrix metalloproteinases; and up regulation of the expression of endothelial adhesion molecules, further amplifying the inflammatory and immune cascade by attracting leukocytes into extravascular tissues.

Interleukin-1 is a naturally occurring cytokine, present in humans and other mammals. Interleukin-1 plays a key role in the inflammatory response and in the immune response. Interleukin-1 receptor antagonist (IL-1 RA) is a naturally occurring molecule which reduces the biologic effects of interleukin-1 by interfering with the binding of IL-1 to its receptor (IL-1 R1, interleukin-1 type 1 receptor). Kineret (Amgen) is a recombinant form of IL-1 RA which is FDA approved for treating rheumatoid arthritis. IL-1 Receptor Type 2 (Amgen), AMG719 (Amgen), and IL-1 Trap (Regeneron), are all biologic inhibitors of interleukin-1.

Etanercept (Enbrel®, Amgen), infliximab (Remicade®), D2E7, CDP 870, and onercept are potent and selective inhibitors of TNF. D2E7, CDP 870, and onercept are in clinical development. Etanercept and infliximab are FDA approved for chronic systemic use to treat rheumatoid arthritis.

Perispinal administration and intranasal administration of cytokine antagonists are new methods of administration of the specific cytokine antagonists of consideration here. These new methods result in improved delivery of these therapeutic molecules to the nervous system, either by local diffusion; by improved transport into the cerebrospinal fluid (CSF); or by direct transport into the CNS. Improved delivery thereby enables these specific cytokine antagonists to produce therapeutic benefit for patients with a variety of neurological and neuropsychiatric disorders.

Clinical Disorders

Patients with the following clinical disorders, among others, will benefit from treatment with cytokine antagonists delivered by the perispinal route or by intranasal administration:

1. Unipolar And Bipolar Affective Disorders

These are disorders of mood, causing recurrent depression and/or recurrent episodes of mood elevation, resulting in mania or hypomania. Current treatment regimens include the use of lithium carbonate, carbamazepine, or anti-psychotic medication. Inflammatory cytokines are involved in the regulation of sleep and mood. In the present invention, perispinal administration of TNF antagonists or IL-1 antagonists is used for the acute or chronic treatment of these disorders. Clinical experience has demonstrated the rapid beneficial effect, and the lasting beneficial effect, of this method of treatment for these disorders. Acute administration of a TNF antagonist results in rapid improvement in affect and cognitive function. Chronic administration results in decreased lability of mood, increased time intervals between mood swings, and decreased amplitude of mood swings. Chronic administration may require twice weekly dosing, but in some patients will be effective when given much less often, sometimes as little as once per three months. Some patients may only require a single dose given at the onset of a mood disturbance. Sleep improvement and improvement in cognition is noted by patients responding to treatment.

2. Schizoaffective Illness

These patients have a thought disorder as well as a mood disorder. These patients can be difficult to distinguish from patients with pure schizophrenia or bipolar affective disorder. Most require treatment with anti-psychotic medication. Some will respond to treatment with lithium carbonate. These patients respond to treatment with the cytokine antagonists of consideration here delivered by the perispinal route. Treatment can be acute or chronic, as outlined in the discussion of unipolar and bipolar affective disorder.

3. Schizophrenia

Schizophrenia is a thought disorder prevalent throughout the world, affecting about 1% of the world's population. Paranoid schizophrenia is a common clinical type. Treatment is almost uniformly unsuccessful. Chronic treatment with neuroleptic medication is usually required with less than satisfactory results These patients have a disturbance in cytokine patterns, which is amenable to treatment with TNF or IL-1 antagonists by perispinal administration or by intranasal administration. Treatment can be acute or chronic, as outlined in the discussion of unipolar and bipolar affective disorder.

4. Depression

Clinical depression is characterized by depressed mood, often accompanied by additional clinical manifestations, such as sleep disturbance, weight loss, loss of appetite, apathy, anhedonia, and when severe, can be associated with suicidal ideation. It is currently treated, when indicated, with antidepressant medication, most commonly selective serotonin reuptake inhibitors (SSRIs) or tricyclic antidepressants. Post-partum depression can be especially serious, occurring after childbirth. Depression, even when treated, is associated with an increased suicide risk. These patients have a disturbance in cytokine patterns, which is amenable to treatment with TNF or IL-1 antagonists by perispinal administration or by intranasal administration. Clinical experience has demonstrated the rapid beneficial effect, and the lasting beneficial effect, of this method of treatment for these disorders. Treatment can be acute or chronic, as outlined in the discussion of unipolar and bipolar affective disorder.

5. Autism

This is an incapacitating, lifelong cognitive developmental disability which usually appears in early childhood. There is no reasonably effective treatment regimen. These patients have a disturbance in cytokine patterns, which is amenable to treatment with TNF or IL-1 antagonists by perispinal administration or by intranasal administration.

6. Anorexia Nervosa

Anorexia Nervosa is an eating disorder characterized by refusal to maintain body weight above a minimally normal weight (usually defined as 85% of expected), combined with a disturbance in the way one's weight or body shape is experienced and intense fear of gaining weight. This is associated with a disturbance in cytokine patterns, which is amenable to treatment with TNF or IL-1 antagonists by perispinal administration or by intranasal administration. Clinical experience has demonstrated weight gain as a result of the use of TNF antagonists.

7. Obsessive-Compulsive Disorder (OCD)

OCD is an anxiety disorder characterized by persistent intrusive thoughts that can only be alleviated by patterns of rigid and ceremonial behavior. Traditional treatment may include the use of SSRIs but is often unsuccessful. These patients have a disturbance in cytokine patterns, which is amenable to treatment with TNF or IL-1 antagonists by perispinal administration or by intranasal administration.

8. Narcotic Addiction

People attempting to discontinue the use of narcotics have great difficulty without pharmacologic assistance if they have been using the narcotics chronically at high dosage levels. Chronic narcotic use creates significant physiological changes in the CNS. These patients have a disturbance in cytokine patterns, which is amenable to treatment with TNF or IL-1 antagonists by perispinal administration or by intranasal administration.

9. Alcohol Withdrawal

People attempting to discontinue the use of alcohol have great difficulty without pharmacologic assistance if they have been consuming large amounts of alcohol on a chronic basis. Both chronic alcohol use and alcohol withdrawal create significant physiological changes in the CNS. These patients have a disturbance in cytokine patterns, which is amenable to treatment with TNF or IL-1 antagonists by perispinal administration or by intranasal administration.

10. Smoking Cessation/Nicotine Withdrawal

People attempting to stop smoking tobacco have great difficulty without pharmacologic assistance. Tobacco smoke contains nicotine, which, on a chronic basis, has potent biologic effects. Smoking cessation and the accompanying nicotine withdrawal creates significant physiological changes in the CNS. These patients have a disturbance in cytokine patterns, which is amenable to treatment with TNF or IL-1 antagonists by perispinal administration or by intranasal administration.

11. Degenerative Disorders, Including Parkinson's Disease, Alzheimer's Disease, Idiopathic Dementia and ALS These chronic neurological disorders include but are not limited to Alzheimer's Disease, Pick's Disease, Creutzfeldt-Jacob Disease (CJD), Variant CJD, Parkinson's Disease, Lewy Body Disease, Idiopathic Dementia, Amyotrophic Lateral Sclerosis (ALS), and the Muscular Dystrophies. Alzheimer's Disease, Pick's Disease, CJD, Lewy Body Disease, Idiopathic Dementia and Variant CJD are all irreversible, progressive forms of dementia. ALS is a progressive motor neuron disease of unknown etiology characterized by progressive weakness. The muscular dystrophies are a group of related neuromuscular disorders which result in progressive loss of muscular function. The exact causation of all of these disorders is uncertain, and there are no curative treatment regimens currently available. Many of these disorders involve CNS, neuronal, or muscular inflammation, and many also involve accelerated neuronal apoptosis. Treatment of these disorders with TNF antagonists or IL-1 antagonists by perispinal administration and/or intranasal administration leads to clinical improvement and/or slowing of disease progression. Chronic treatment regimens are necessary, with doses usually administered at an interval varying from twice per week to once per month. Clinical experience has demonstrated the beneficial effect of this method of treatment for these disorders.

12. Spinal Cord Injury

About 10,000 cases occur per year in the U.S., with a current population of over 200,000 patients with residual neurologic damage, many of whom are paralyzed (quadriplegia or paraplegia). Current treatment for the acute injury is inadequate. In the early 1990's it was shown that early (within 8 hours of injury) treatment with high doses of steroids (methyl prednisolone) was beneficial for some of these patients. Surgical stabilization and spinal decompression is often necessary because of excessive swelling (edema) which can itself cause further severe injury to the cord due to further compression of the cord against its bony spinal canal. The etiology of most of these cases are motor vehicle accidents, with the remainder being sports injuries, falls, and other accidents. The window of opportunity for treatment is small, since massive swelling can occur within minutes. The use of a cytokine antagonist, delivered by perispinal administration, ameliorates neurological damage caused by acute spinal cord injury, and is also beneficial for patients with chronic spinal cord injury. Treatment with TNF antagonists or IL-1 antagonists given parenterally by perispinal administration leads to clinical improvement. Clinical experience has demonstrated the beneficial effect of this method of treatment for these disorders.

13. Headache Syndromes, including Migraine Headaches and Cluster Headaches

Elevated levels of inflammatory cytokines are found in patients with severe neurologic headache syndromes, including, but not limited to migraine headaches and cluster headaches. Migraine headaches, a form of vascular headache, are common, and may have associated neurologic symptoms, such as visual disturbance, photophobia, and, in rare instances, can be associated with stroke. Treatment of these disorders with TNF antagonists or IL-1 antagonists by perispinal administration leads to clinical improvement. Treatment regimens can be either acute or chronic, and will vary with the clinical setting. Clinical experience has demonstrated the beneficial effect of this method of treatment for these disorders, often with rapid diminution of headache pain demonstrated.

14. Neuropathic Pain

TNF has been found to be of central importance in the pathogenesis of several types of neuropathic pain, including, but not limited to spinal radiculopathy, nerve root inflammation due to intervertebral disc herniation, and neuropathy associated with chronic constriction injury. There are many other forms of neuropathic pain, defined generally as pain initiated or caused by a primary lesion or dysfunction in the nervous system. Treatment of these disorders with TNF antagonists or IL-1 antagonists by perispinal administration leads to clinical improvement. Treatment regimens can be either acute or chronic, and will vary with the clinical setting. Clinical experience has demonstrated the beneficial effect of this method of treatment for several different forms of neuropathic pain.

15. Lumbar And Cervical Radiculopathy

Inflammation of the nerve roots in the lumbar or cervical region may lead to neurologic dysfunction. These forms of radiculopathy commonly result in pain in a nerve root distribution, often with sensory dysfunction characterized by numbness and/or paresthesia. A smaller subset of these patients also experience motor weakness. TNF has been strongly implicated in the pathogenesis of these clinical syndromes. Release of TNF from damaged intervertebral discs, as the result of disc herniation or other forms of disc disease has been suggested to be the central causative factor. Clinical experience has established the efficacy of treatment of these disorders with TNF antagonists delivered by perispinal administration.

16. Fibromyalgia

Fibromyalgia is a syndrome of unknown cause that results in chronic, widespread neuromuscular pain and fatigue, often with multiple, tender areas, sleep disturbance, and additional clinical symptoms. Clinical experience has established the efficacy of treatment of patients with this diagnosis utilizing TNF antagonists delivered by perispinal administration. Treatment with TNF antagonists or IL-1 antagonists given parenterally by perispinal administration leads to clinical improvement.

17. Low Back Pain

Low back pain (LBP) can result from a wide variety of clinical conditions. Many forms of LBP are mild or spontaneously resolve. Other types are severe, treatment refractory, and can either be acute, subacute or chronic. Many of these patients have been diagnosed with intervertebral disc disease, ranging from a solitary annular tear of one disc capsule, to a mild disc bulge, to multiple large disc herniations present in a single individual. Clinical experience has established the efficacy of treatment of patients with these disc disorders through the use of TNF antagonists delivered by perispinal administration. In addition this method of treatment has been beneficial for other patients with back pain, including those patients with apparently normal MRI examination of the spine. Many of these patients may have undiagnosed annular tears of their intervertebral disc capsules, or other forms of internal disc derangement. Treatment with TNF antagonists or IL-1 antagonists given parenterally by perispinal administration leads to clinical improvement.

18. Post-Herpetic Neuralgia

Persistent severe pain following herpes zoster can be chronic and treatment refractory, particularly with patients over the age of 65. Inflammation in the dorsal root ganglion, continuing after the healing of cutaneous lesions, has been documented. Treatment with TNF antagonists, administered by the perispinal route, in conjunction with orally administered anti-viral therapy, such as famciclovir, helps alleviate this form of neuropathic pain. Treatment with TNF antagonists or IL-1 antagonists given parenterally by perispinal administration leads to clinical improvement. Clinical experience has confirmed the beneficial effect of this treatment modality.

19. Vertebral Disc Disease

Disease of one or more intervertebral discs can be the result of trauma, aging, arthritis, or other inflammatory disorders. The resulting damage can produce disruption of the capsule of the disc, allowing release of TNF into the extradiscal space. This may result in TNF-mediated neurotoxicity, inflammation, and resulting neuropathic pain and/or sensory and motor neuropathy or radiculopathy. These patients may have frank disc herniation, or more subtle forms of disc disruption, such as disc bulging, disc protrusion, or annular tear of the disc capsule. Many of these patients are diagnosed as having degenerative disc disease. Treatment with TNF antagonists or IL-1 antagonists given parenterally by perispinal administration leads to clinical improvement. Extensive clinical experience has documented the favorable effect of this method of treatment for patients in this clinical category.

20. Chronic Fatigue Syndrome (CFS)

Patients with CFS have severe chronic fatigue of six months or longer duration, with known causes excluded; and have additional symptoms, including memory impairment, sore throat, adenopathy, myalgias, arthralgias, and sleep disturbance. Treatment with TNF antagonists or IL-1 antagonists by perispinal administration or intranasal administration leads to clinical improvement. Clinical experience has documented the favorable effect of this method of treatment for patients with this diagnosis.

21. Reflex Sympathetic Dystrophy (RSD)

RSD is a chronic pain syndrome characterized by chronic, severe, treatment refractory neuropathic pain of unknown etiology, but often associated with a pre-existing injury, and often accompanied by skin and joint changes and diminished motor function in the involved extremity. Inflammatory cytokines are involved in the pathophysiology. Treatment with TNF antagonists or IL-1 antagonists given parenterally by perispinal administration leads to clinical improvement.

Dosages and Routes of Administration

The dosage of a cytokine antagonist used for perispinal administration will in general be within one order of magnitude of the dosage used as a single dose for systemic administration. For example, if the usual dose when administered systemically is 100 mg, then the dose used for perispinal administration will usually be between 10 mg and 100 mg. The exception to this general guideline occurs with intrathecal injections or intranasal administration, where the required dosage is smaller, usually in the range of 1% to 10% of the corresponding systemic dose for the intrathecal route, and usually in the range of 10% to 25% for the intranasal route.

For the treatment of acute or severe conditions, the dose will generally be adjusted upward. In the above example the dose selected would therefore be 100 mg, rather than 10 mg, if the condition were acute and/or severe.

Localized perilesional injection can allow the use of subcutaneous administration even in the case when the medication is normally administered intravenously. An example of this would be the use of infliximab subcutaneously in the interspinous area for the treatment of nerve root inflammation associated with intervertebral disc disease.

For treating the above diseases with the above mentioned TNF antagonists, these TNF antagonists may be administered by the following routes:

The above TNF antagonists may be administered subcutaneously in the human and the dosage level is in the range of 1 mg to 300 mg per dose, with dosage intervals as short as one day.

The above TNF antagonists may be administered intramuscularly in the human and the dosage level is in the range of 1 mg to 200 mg per dose, with dosage intervals as short as two days.

The above TNF antagonists may be administered epidurally in the human and the dosage level is in the range of 1 mg to 300 mg per dose, with dosage intervals as short as two days.

The above TNF antagonists may be administered peridurally in the human and the dosage level is in the range of 1 mg to 300 mg per dose, with dosage intervals as short as two days.

The above TNF antagonists may be administered by interspinous injection in the human and the dosage level is in the range of 1 mg to 300 mg per dose, with dosage intervals as short as two days.

The above TNF antagonists may be administered by intranasal administration utilizing a nasal spray or nasal inhaler in the human and the dosage level is in the range of 1 mg to 50 mg per dose, with dosage intervals as short as four hours.

Interleukin-1 antagonists are administered in a therapeutically effective dose, which will generally be 10 mg to 200 mg per dose. The dosage interval will be as short as once daily.

ADVANTAGES OF THE PRESENT INVENTION

Accordingly, an advantage of the present invention is that it provides for the localized administration of specific biologics as a new pharmacologic treatment of neurological and neuropsychiatric diseases and disorders; such that the use of these cytokine antagonists will result in the amelioration of these conditions.

Another advantage of the present invention is that it provides for specific biologics delivered by anatomically localized administration, which, when compared to systemic administration, produces one or more of the following: greater efficacy; more rapid onset; longer duration of action; improved delivery to the CNS; or fewer side effects.

Another advantage of the present invention is that it provides for specific biologics for providing suppression and inhibition of the action of cytokines in a human to treat neurological and neuropsychiatric diseases and disorders.

Another advantage of the present invention is that it provides for specific biologics administered by specific methods for treating humans with neurological and neuropsychiatric diseases and disorders which due to their biologic action will produce clinical improvement in the patient and will give the patient a better opportunity to heal, slow disease progression, prevent neurological damage, reduce pain, or otherwise improves the patient's health.

Another advantage of the present invention is that it provides for specific biologics, including cytokine antagonists to tumor necrosis factor alpha or to interleukin-1, using localized administration, including perispinal administration, as the preferred form of administration, for the treatment of neurological disorders, including dementia, low back pain, and neuropathic pain.

Another advantage of the present invention is that it provides for specific biologics, including cytokine antagonists to tumor necrosis factor alpha or to interleukin-1, using localized administration, including perispinal administration or intranasal administration, as the preferred form of delivery, for the treatment of neuropsychiatric disorders, including depression, schizophrenia, anorexia nervosa and chronic fatigue syndrome.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

GENERAL REFERENCES

[1]. Bathon J M, Martin R W, Fleischmann R M, et al. A comparison of etanercept and methotrexate in patients with early rheumatoid arthritis. N Engl J Med (2000); 343:1586-1593.

[2]. Mease P J, Goffe B S, Metz J, VanderStoep A, Finck B, Burge D J. Etanercept in the treatment of psoriatic arthritis and psoriasis: a randomised trial. Lancet. (2000) July 29; 356(9227):385-90.

[3]. Gorman J D, Sack K E, David J C. Treatment of ankylosing spondylitis by inhibition of tumor necrosis factor-alpha. N Engl J Med (2000); 346:1349-1356.

[4]. Moreland L W, Schiff M H, Baumgarner S W, et al. Etanercept therapy in rheumatoid arthritis: a randomized, controlled trial. N Engl J Med (1999); 130:478-486.

[5]. Weinblatt M E, Kremer J M, Bankhurst A D, et al. A trial of etanercept, a recombinant tumor necrosis factor receptor:Fc Fusion protein, in patients with rheumatoid arthritis receiving methotrexate. N Engl J Med (1999); 340(4):253-259.

[6]. Lovell D J, Giannini E H, Reiff A, et al. Etanercept in children with polyarticular juvenile rheumatoid arthritis. N Engl J Med (2000); 342:763-769.

What is claimed is:

1. A method for delivering etanercept to a human, comprising:
administering etanercept to said human by perispinal injection without direct intrathecal or epidural injection.

2. A method for delivering etanercept to the cerebrospinal fluid of a human, comprising: administering etanercept to said human by perispinal injection without direct intrathecal or epidural injection.

* * * * *

UNITED STATES PATENT AND TRADEMARK OFFICE
CERTIFICATE OF CORRECTION

PATENT NO. : 8,119,127 B2  
APPLICATION NO. : 11/262528  
DATED : February 21, 2012  
INVENTOR(S) : Tobinick It is certified that error appears in the above-identified patent and that said Letters Patent is hereby corrected as shown below:

On the title page of the patent, please delete the following paragraph in item "(60)":

"Division of application No. 10/269,745, filed on Oct. 9, 2002, now Pat. No. 6,982,089, which is a continuation-in-part of application No. 10/236,097, filed on Sep. 6, 2002, now abandoned, which is a continuation-in-part of application No. 09/841,844, filed on Apr. 25, 2001, now Pat. No. 6,537,549, which is a continuation-in-part of application No. 09/826,976, filed on Apr. 5, 2001, now Pat. No. 6,419,944, which is a continuation-in-part of application No. 09/666,068, filed Dec. 11, 2000, now Pat. No. 6,379,666, which is a divisional of application No. 09/476,643, filed on Dec. 31, 1999, now Pat. No. 6,177,077, which is a continuation-in-part of application No, 09/275,070, filed on Mar. 23, 1999, now Pat. No. 6,015,557, which is a continuation-in-part of application No. 09/256,388, filed on Feb. 24, 1999, now abandoned."

and insert therefore:

-- Division of application No. 10/269,745, filed on Oct. 9, 2002, now Pat. No. 6,982,089, which is a continuation-in-part of application No, 10/236,097, filed on Sep. 6. 2002, now abandoned, which is a continuation-in-part of application No. 09/841,844, filed on Apr. 25, 2001, now Pat. No. 6,537,549, which is a continuation-in-part of application No. 09/826,976, filed on Apr, 5, 2001, now Pat. No. 6,419,944, which is a continuation-in-part of application No. 09/866,068, filed Dec. 11, 2000, now Pat. No. 6,379,666, which is a divisional of application No. 09/476,643, filed on Dec. 31, 1999, now Pat. No. 6,177,077, which is a continuation-in-part of application No. 09/275,070, filed on Mar. 23, 1999, now Pat. No. 6,015,557, which is a continuation-in-part of application No. 09/256,388, filed on Feb. 24, 1999, now abandoned; and application Ser. No. 10/289,745, filed on Oct. 9, 2002, now U.S. Pat. No. 6,982,089, is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/666,068, filed on December 11, 2000, now U.S. Pat. No. 6,379,666, which is a divisional of application Ser. No. 09/476,643, filed Dec. 31, 1999, now U.S. Pat No. 6,177,077, which is a continuation-in-part of application Ser. No. 09/275,070, filed March 23, 1999, now U.S. Pat No. 6,015,557, which is a continuation-in-part of application Ser. No. 09/256,388, filed on Feb. 24, 1999, Signed and Sealed this  
Twenty-fifth Day of February, 2014

Michelle K. Lee  
*Deputy Director of the United States Patent and Trademark Office*

CERTIFICATE OF CORRECTION (continued)
U.S. Pat. No. 8,119,127 B2 now abandoned. --

In the Specification

In column 1, lines 6-23, please delete the following paragraph:

"This application is a divisional of U.S. application Ser. No. 10/269,745, filed on Oct. 9, 2002, now U.S. Pat. No. 6,982,089, which is a continuation-in-part of application Ser. No, 10/236,097, filed on Sep. 6, 2002, now abandoned, which is a continuation-in-part of application Ser. No. 09/841,844, filed on Apr. 25, 2001, now U.S. Pat No. 6,537,549, which is a continuation-in-part of application Ser. No. 09/826,976, filed on Apr. 5, 2001, now U.S. Pat. No. 6,419,944, which is a continuation-in-part of Ser. No. 09/666,088, filed Dec. 11, 2000, now U.S. Pat. No. 6,379,666, which is a divisional of application Ser. No, 09/476,643, filed on Dec. 31, 1999, now U.S. Pat. No. 6,177,077, which is a continuation-in-part of application Ser. No. 09/275,070, filed on Mar. 23, 1999, now U.S. Pat. No. 6,015,557, which is a continuation-in-part of application Ser. No. 09/256,388, filed on Feb. 24, 1999, now abandoned."

and insert therefore:

-- This application Ser. No. 11/262,528 is a divisional of U.S. application Ser. No. 10/269,745, filed on Oct. 9, 2002, now U.S. Pat. No. 6,982,089, which is a continuation-in-part of application Ser. No. 10/236,097, filed on Sep. 6, 2002, now abandoned, which is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/666,068, filed Dec. 11, 2000, now U.S. Pat. No. 6,379,666, which is a divisional of application Ser. No. 09/476,643, filed on Dec. 31, 1999, now U.S. Pat. No. 6,177,077, which is a continuation-in-part of application Ser. No. 09/275,070, filed on Mar. 23, 1999, now U.S. Pat. No. 6,015,557, which is a continuation-in-part of application Ser. No. 09/256,388, filed on Feb. 24, 1999, now abandoned; and application Ser. No. 10/269,745, filed on Oct. 9, 2002, now U.S. Pat No. 6,982,089, is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/666,068, filed on December 11, 2000, now U.S. Pat. No. 6,379,666, which is a divisional of application Ser. No. 09/476,643, filed Dec. 31, 1999, now U.S. Pat No. 6,177,077, which is a continuation-in-part of application Ser. No. 09/275,070, filed March 23, 1999, now U.S. Pat. No. 6,015,557, which is a continuation-in-part of application Ser. No. 09/256,388, filed on Feb. 24, 1999, now abandoned. --

UNITED STATES PATENT AND TRADEMARK OFFICE
CERTIFICATE OF CORRECTION

Page 1 of 2

PATENT NO. : 8,119,127 B2
APPLICATION NO. : 11/262528
DATED : February 21, 2012
INVENTOR(S) : Tobinick It is certified that error appears in the above-identified patent and that said Letters Patent is hereby corrected as shown below:

On the title page of the patent, please delete the following paragraph in item "(60)":

"Division of application No. 10/269,745, filed on Oct. 9, 2002, now Pat. No. 6,982,089, which is a continuation-in-part of application No. 10/236,097, filed on Sep. 6, 2002, now abandoned, which is a continuation-in-part of application No. 09/841,844, filed on Apr. 25, 2001, now Pat. No. 6,537,549, which is a continuation-in-part of application No. 09/826,976, filed on Apr. 5, 2001, now Pat. No. 6,419,944, which is a continuation-in-part of application No. 09/666,068, filed Dec. 11, 2000, now Pat. No. 6,379,666, which is a divisional of application No. 09/476,643, filed on Dec. 31, 1999, now Pat. No. 6,177,077, which is a continuation-in-part of application No, 09/275,070, filed on Mar. 23, 1999, now Pat. No. 6,015,557, which is a continuation-in-part of application No. 09/256,388, filed on Feb. 24, 1999, now abandoned."

and insert therefore:

-- Division of application No. 10/269,745, filed on Oct. 9, 2002, now Pat. No. 6,982,089, which is a continuation-in-part of application No, 10/236,097, filed on Sep. 6. 2002, now abandoned, which is a continuation-in-part of application No. 09/841,844, filed on Apr. 25, 2001, now Pat. No. 6,537,549, which is a continuation-in-part of application No. 09/826,976, filed on Apr, 5, 2001, now Pat. No. 6,419,944, which is a continuation-in-part of application No. 09/666,068, filed Dec. 11, 2000, now Pat. No. 6,379,666, which is a divisional of application No. 09/476,643, filed on Dec. 31, 1999, now Pat. No. 6,177,077, which is a continuation-in-part of application No. 09/275,070, filed on Mar. 23, 1999, now Pat. No. 6,015,557, which is a continuation-in-part of application No. 09/256,388, filed on Feb. 24, 1999, now abandoned; and application Ser. No. 10/269,745, filed on Oct. 9, 2002, now U.S. Pat. No. 6,982,089, is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of This certificate supersedes the Certificate of Correction issued February 25, 2014.

Signed and Sealed this
Twenty-second Day of April, 2014

Michelle K. Lee
*Deputy Director of the United States Patent and Trademark Office* application Ser. No. 09/666,068, filed on December 11, 2000, now U.S. Pat. No. 6,379,666, which is a divisional of application Ser. No. 09/476,643, filed Dec. 31, 1999, now U.S. Pat No. 6,177,077, which is a continuation-in-part of application Ser. No. 09/275,070, filed March 23, 1999, now U.S. Pat No. 6,015,557, which is a continuation-in-part of application Ser. No. 09/256,388, filed on Feb. 24, 1999, now abandoned. --

In the Specification

In column 1, lines 6-23, please delete the following paragraph:

"This application is a divisional of U.S. application Ser. No. 10/269,745, filed on Oct. 9, 2002, now U.S. Pat. No. 6,982,089, which is a continuation-in-part of application Ser. No, 10/236,097, filed on Sep. 6, 2002, now abandoned, which is a continuation-in-part of application Ser. No. 09/841,844, filed on Apr. 25, 2001, now U.S. Pat No. 6,537,549, which is a continuation-in-part of application Ser. No. 09/826,976, filed on Apr. 5, 2001, now U.S. Pat. No. 6,419,944, which is a continuation-in-part of Ser. No. 09/666,088, filed Dec. 11, 2000, now U.S. Pat. No. 6,379,666, which is a divisional of application Ser. No, 09/476,643, filed on Dec. 31, 1999, now U.S. Pat. No. 6,177,077, which is a continuation-in-part of application Ser. No. 09/275,070, filed on Mar. 23, 1999, now U.S. Pat. No. 6,015,557, which is a continuation-in-part of application Ser. No. 09/256,388, filed on Feb. 24, 1999, now abandoned."

and insert therefore:

-- This application Ser. No. 11/262,528 is a divisional of U.S. application Ser. No. 10/269,745, filed on Oct. 9, 2002, now U.S. Pat. No. 6,982,089, which is a continuation-in-part of application Ser. No. 10/236,097, filed on Sep. 6, 2002, now abandoned, which is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/666,068, filed Dec. 11, 2000, now U.S. Pat. No. 6,379,666, which is a divisional of application Ser. No. 09/476,643, filed on Dec. 31, 1999, now U.S. Pat. No. 6,177,077, which is a continuation-in-part of application Ser. No. 09/275,070, filed on Mar. 23, 1999, now U.S. Pat. No. 6,015,557, which is a continuation-in-part of application Ser. No. 09/256,388, filed on Feb. 24, 1999, now abandoned; and application Ser. No. 10/269,745, filed on Oct. 9, 2002, now U.S. Pat No. 6,982,089, is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/666,068, filed on December 11, 2000, now U.S. Pat. No. 6,379,666, which is a divisional of application Ser. No. 09/476,643, filed Dec. 31, 1999, now U.S. Pat No. 6,177,077, which is a continuation-in-part of application Ser. No. 09/275,070, filed March 23, 1999, now U.S. Pat. No. 6,015,557, which is a continuation-in-part of application Ser. No. 09/256,388, filed on Feb. 24, 1999, now abandoned. --